(12) United States Patent
Zhang et al.

(10) Patent No.: US 11,649,343 B2
(45) Date of Patent: May 16, 2023

(54) ENHANCING BOND STRENGTH OF MEDICAL DEVICES

(71) Applicant: Becton, Dickinson and Company, Franklin Lakes, NJ (US)

(72) Inventors: Jianbin Zhang, Livingston, NJ (US); Theresa Hermel-Davidock, Vernon Hills, IL (US); Edward Bryan Coughlin, Amherst, MA (US); Tea Datashvili, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/012,932

(22) Filed: Sep. 4, 2020

(65) Prior Publication Data

US 2020/0399457 A1    Dec. 24, 2020

Related U.S. Application Data

(63) Continuation of application No. 15/711,657, filed on Sep. 21, 2017, now abandoned.

(60) Provisional application No. 62/399,748, filed on Sep. 26, 2016.

(51) Int. Cl.
| | |
|---|---|
| *C08L 23/20* | (2006.01) |
| *A61L 27/16* | (2006.01) |
| *C08L 23/06* | (2006.01) |
| *C08L 23/12* | (2006.01) |
| *F16L 13/10* | (2006.01) |

(52) U.S. Cl.
CPC ........... *C08L 23/20* (2013.01); *A61L 27/16* (2013.01); *C08L 23/06* (2013.01); *C08L 23/12* (2013.01); *F16L 13/103* (2013.01); *C08L 2203/18* (2013.01)

(58) Field of Classification Search
CPC .... C08L 23/20; C08L 51/00–08; C08L 23/06; C08L 23/12; C08L 2207/04
See application file for complete search history.

(56) References Cited

U.S. PATENT DOCUMENTS

| | | |
|---|---|---|
| 3,029,216 A | 4/1962 | Bailey, Jr. et al. |
| 3,978,855 A | 9/1976 | McRae |
| 4,727,120 A | 2/1988 | Nogues |
| 4,960,594 A | 10/1990 | Honeycutt |
| 5,214,091 A | 5/1993 | Tanaka et al. |

(Continued)

FOREIGN PATENT DOCUMENTS

| | | |
|---|---|---|
| CA | 2383117 A1 | 3/2001 |
| CN | 101055422 A | 10/2007 |

(Continued)

OTHER PUBLICATIONS

SciFinder search, American Chemical Society, 2015, 20 pages.

(Continued)

*Primary Examiner* — Michael M Dollinger
(74) *Attorney, Agent, or Firm* — Servilla Whitney LLC

(57) ABSTRACT

Components of medical devices include polypropylene-poly (ethylene oxide) amphiphilic graft copolymers (PP-g-PEO) in their base polymer formulations. The base polymeric formulations comprise at least a polymer or co-polymer of propylene. These components are suitable for solvent-bonding with other components and enhance bond strength of the medical devices.

16 Claims, 5 Drawing Sheets

(56) References Cited

U.S. PATENT DOCUMENTS

| | | | |
|---|---|---|---|
| 5,292,803 A | 3/1994 | Ohmae et al. | |
| 5,424,150 A | 6/1995 | Ohnishi et al. | |
| 6,238,408 B1 | 5/2001 | Kawabata | |
| 6,303,200 B1 | 10/2001 | Woo et al. | |
| 6,433,080 B1 | 8/2002 | Fujiki et al. | |
| 6,613,187 B1 | 9/2003 | Ding et al. | |
| 6,649,681 B2 | 11/2003 | Rohn et al. | |
| 6,673,192 B1 | 1/2004 | Woods et al. | |
| 7,094,837 B1 * | 8/2006 | Ellul | C08L 23/12 525/193 |
| 7,994,253 B2 * | 8/2011 | Jacob | C08L 23/16 428/220 |
| 8,722,962 B2 | 5/2014 | Dera et al. | |
| 9,150,674 B2 | 10/2015 | Hermel-Davidock et al. | |
| 9,714,309 B2 * | 7/2017 | Hermel-Davidock | C08L 23/06 |
| 10,336,852 B2 * | 7/2019 | Hermel-Davidock | C08G 65/2603 |
| 2004/0034184 A1 | 2/2004 | Takashima et al. | |
| 2008/0273820 A1 | 11/2008 | Wiker et al. | |
| 2009/0258209 A1 * | 10/2009 | Jacob | C08L 23/16 264/328.18 |
| 2010/0111167 A1 | 5/2010 | Wu et al. | |
| 2011/0251596 A1 | 10/2011 | Kim | |
| 2012/0005930 A1 | 1/2012 | Cragg | |
| 2014/0058045 A1 | 2/2014 | Hermel-Davidock et al. | |
| 2015/0018791 A1 | 1/2015 | Devenish et al. | |

FOREIGN PATENT DOCUMENTS

| | | |
|---|---|---|
| JP | 50-112494 A | 9/1975 |
| JP | 5232796 B2 | 7/2013 |
| WO | 87/05206 A1 | 9/1987 |
| WO | 01/18112 A2 | 3/2001 |
| WO | 2014/159419 A1 | 10/2014 |
| WO | 2015/032817 A1 | 3/2015 |
| WO | 2016007438 A1 | 1/2016 |

OTHER PUBLICATIONS

"Pebax In Medical Applications", 2 pgs.

PCT International Search Report and Written Opinion in PCT/US2017/052931 dated Jan. 23, 2018, 12 pages.

Winter, H. Henning, et al., "Rigid Pore Structure from Highly Swollen Polymer Gels", Macromolecules 35, 2002, 3325-3327.

Sirkar, Kamalesh K., "Membranes, Phase Interfaces, and Separations: Novel Techniques and Membranes—An Overview", Ind. Eng. Chem. Res. 47, 2008, 5250-5266.

Chen, John C., et al., "Break-Through in Breathable Polymers: Morphology, Properties, and Performance", Dupont, Wilmington, DE, 1-8.

Gugliuzza, A., et al., "Role of additives in the water vapor transport through block co-poly(amide/ether) membranes: effects on surface and bulk polymer properties", European Polymer Journal 40, 2004, 2381-2389.

Jeon, Hyun K., et al., "Premade vs. reactively formed compatibilizers for PMMA/PS melt blends", Polymer 46, (2005), pp. 12422-12429.

Johnson, Larry, et al., "Breathable TPE Films for Medical Applications", MDDI Medical Device and Diagnostic Industry News Products and Suppliers, Jul. 2000, 6 pages.

Jones, Mitchell Lawrence, et al., "Antimicrobial properties of nitric oxide and its application in antimicrobial formulations and medical devices", Appl Microbiol Biotechnol (2010), 88: 401-407.

Jonquieres, Anne, et al., "Permeability of block copolymers to vapors and liquids", Prog. Polym. Sci. 27, 2002, 1803-1877.

Lowe, A., et al., "Electrospun nitric oxide releasing bandage with enhanced wound healing", Acta Biomaterialia 13 (2015), pp. 121-130.

Seabra, Amedea B., et al., "Polynitrosated Polyesters: Preparation, Characterization, and Potential Use for Topical Nitric Oxide Release", Biomacromolecules 2005, 6, pp. 2512-2520.

Metz, S. J., et al., "Gas-Permeation Properties of Poly(ethylene oxide) Poly(butylene terephthalate) Block Copolymers", Macromolecules 37, 2004, 4590-4597.

Metz, S. J., et al., "Water vapor and gas transport through a poly(butylene terephthalate) poly(ethylene oxide) block copolymer". Desalination 148, 2002, 303-307.

Mueller, Chad, et al., "Breathable Polymer Films Produced by the Microlayer Coextrusion Process", Journal of Applied Polymer Science, vol. 78, 2000, 816-828.

Nandi, Souvik, et al., "Open-pore morphology of i-PP copolymer crystallized from a gel state in supercritical propane", Polymer 45, 2004, 4819-4827.

Safety Data Sheet for R01 C-01. IN EOS Olefins and Polymer USA. Available at https://www.ineos.com/show-document/?grade=RO 1C-01 &bu= IN EOS+0+%26+ P+ U SA&documentType=S DS&doc Language= EN &version=927 c41a7f72842dc9dfe3e8a978b47b1 (Year: 2014).

\* cited by examiner

ENHANCING BOND STRENGTH OF MEDICAL DEVICES

CROSS-REFERENCE TO RELATED APPLICATIONS

This application is a continuation of U.S. patent application Ser. No. 15/711,657, filed on Sep. 21, 2017, which claims priority under 35 U.S.C. § 119(e) to U.S. Provisional Application No. 62/399,748, filed Sep. 26, 2016, the disclosures of which are incorporated herein by reference in their entireties.

TECHNICAL FIELD

Principles and embodiments of the present invention relate generally to medical devices including polypropylene-poly(ethylene oxide) amphiphilic graft copolymers (PP-g-PEO) in their base polymer formulations. Specifically, including PP-g-PEO in formulations for ethylene- and/or propylene-containing polyolefin or thermoplastic elastomer (TPE) tubing enhances bonding strength between the tubing and connectors, where the connectors are made of different materials compared to the tubing.

BACKGROUND

Medical tubing made from polyolefin (e.g., ethylene-or propylene-containing) or thermoplastic elastomer (TPE) materials are used in, for example, infusion sets for delivery of intravenous (IV) fluids. Connectors are bonded to the tubing, thereby forming medical devices, which may be used alone or in conjunction with other medical devices to, for example, deliver fluids.

Solvent bonding is a technique used for joining molded plastic parts of medical devices. During the bonding process, the solvent dissolves the surface of two mating parts and allows the material to flow together. Once the solvent evaporates, the result is a material-to-material bond. Many parts of medical devices made from plastics can be solvent-bonded in an application where ultrasonic bonding does not work. For dissimilar materials, however, solvent bonding does not typically achieve a satisfactory bonding. Namely, due to hydrophobicity and low surface energy, the polyolefins and thermoplastic elastomers (TPEs) demonstrate poor interaction and solvent bonding with connector materials that are typically made from poly(methyl methacrylate) (PMMA), styrene maleic anhydride (SMA), polycarbonate (PC), and methyl methacrylate-acrylonitrile-butadiene-styrene (MABS). For certain applications such as an infusion kit with polypropylene or polypropylene-containing-TPE tubing connected with a PMMA or SMA or PC or MABS connector, bonding performance between polypropylene or TPE and the connector has not yet been acceptable. Solvents suitable for solvent bonding processes include those solvents that can partially liquefy plastic along the joint and allow the joint to solidify causing a permanent chemical bonding. It is similar in end result to heat bonding metal or thermoplastic. Bonded joints have an advantage over other adhesives in that there is no third material creating the joint. Joints are also airtight when created properly. Solvent bonding provides an additional advantage in that it more readily integrates into rapid automated assembly processes compared to more conventional adhesives, with a frequent cost advantage as well. Solvents suitable for solvent bonding parts of medical devices are required to be non-flammable, not carcinogenic, and not cause mechanical stress on the parts, an example of which is cyclohexanone.

Attempts have been made to improve bond strength. For example, U.S. Pat. No. 6,613,187 uses a cement composition comprising cyclic olefin-containing polymer and a solvent for solvent-bonding first and second polymeric materials. WO01/18112 also discloses a cement composition that is cyclic olefin containing polymer-based cement composition or bridged polycyclic hydrocarbon containing polymer-based. In addition, WO01/18112 discloses medical products that may be solvent-bonded, the products comprising homopolymers and/or copolymers of cyclic olefin containing polymers and bridged polycyclic hydrocarbon containing polymers (collectively sometimes referred to as "COCs"). U.S. Pat. No. 6,649,681 uses a solvent-based adhesive to bond polymeric fittings to components of articles used in medical applications. U.S. Pat. No. 6,673,192 uses cyanoacrylate adhesives activated with certain multi-amine compounds to bond polyolefin substrates.

There is a continuing need to improve bond strength of medical devices. In particular, there is a need to improve bond strength of medical devices when bonding is done by a solvent, which is not flammable, not carcinogenic, and does not cause mechanical stress of the parts. Due to these solvent requirements, finding materials for components of medical devices that are suitable for solvent-bonding is an on-going challenge.

SUMMARY

Provided are components of medical devices, e.g., tubing, which exhibit enhanced bonding to other components, e.g., connectors.

Various embodiments are listed below. It will be understood that the embodiments listed below may be combined not only as listed below, but in other suitable combinations in accordance with the scope of the invention.

A first aspect is a tubing for a medical device formed from a blend comprising: a base polymeric formulation comprising at least a polymer or co-polymer of ethylene or propylene and excluding free poly(ethylene oxide); and an additive comprising a polypropylene-poly(ethylene oxide) amphiphilic graft copolymer (PP-g-PEO); the PP-g-PEO being present in the blend in an amount in the range of about 0.01 to about 5.0% by weight of the blend.

The base polymeric formulation may comprise polyethylene, polypropylene, a polypropylene-maleic anhydride co-polymer, a polyethylene-polypropylene co-polymer, a polyethylene- and/or polypropylene-containing thermoplastic elastomer (TPE), or combinations thereof. The base polymeric formulation comprises a co-polymer of polyethylene and polypropylene. The polyethylene-and/or polypropylene-containing thermoplastic elastomer (TPE) comprises at least 60 mol % total polyethylene and/or polypropylene. The PP-g-PEO may be a product of ethylene oxide ring-opening polymerization of a polypropylene-maleic anhydride co-polymer (PP-MA) having from 10-50 weight percent of maleic anhydride. In one or more embodiments, the PP-g-PEO is effective to enhance bonding of the tubing to a connector.

Another aspect is a medical device comprising: a tubing comprising a polymeric blend comprising a base polymeric formulation comprising at least a polymer or co-polymer of ethylene or propylene and excluding free poly(ethylene oxide), and an additive comprising a polypropylene-poly(ethylene oxide) amphiphilic graft copolymer (PP-g-PEO), wherein the PP-g-PEO is present in the blend in an amount in the range of about 0.01 to about 5.0% by weight of the blend; and a connector bonded to the tubing wherein the PP-g-PEO is effective to enhance bonding of the tubing to a connector.

The base polymeric formulation may comprise polyethylene, polypropylene, a polyethylene-polypropylene co-polymer, a polyethylene- and/or polypropylene-containing thermoplastic elastomer (TPE), or combinations thereof. The base polymeric formulation may comprise a co-polymer of polyethylene and polypropylene. The polyethylene-and/or polypropylene-containing thermoplastic elastomer (TPE) may comprise at least 60 mol % polyethylene and/or polypropylene. The PP-g-PEO may be a product of ethylene oxide ring-opening polymerization of a polypropylene-maleic anhydride co-polymer (PP-MA) having from 10-50 weight percent of maleic anhydride. The connector may comprise a polar material. The polar material may be selected from the group consisting of: poly(methyl methacrylate) (PMMA), styrene maleic anhydride (SMA), polycarbonate (PC), and methyl methacrylate-acrylonitrile-butadiene-styrene (MABS). The connector may be solvent-bonded to the tubing.

An additional aspect is a method of making a medical device comprising: obtaining a polypropylene-poly(ethylene oxide) amphiphilic graft copolymer (PP-g-PEO); combining the PP-g-PEO with a base polymeric formulation comprising at least a polymer or co-polymer of ethylene or propylene and excluding free poly(ethylene oxide) to form a blend, the PP-g-PEO being present in the blend in an amount in the range of about 0.01 to about 5.0% by weight of the blend; forming a tubing from the blend; bonding the tubing to a connector in the presence of a solvent to form the medical device; wherein the PP-g-PEO is effective to enhance bonding of the tubing to a connector.

Ethylene oxide ring-opening polymerization of a polypropylene-maleic anhydride co-polymer (PP-MA) having from 10-50 weight percent of maleic anhydride may be used to form the PP-g-PEO.

DETAILED DESCRIPTION

Figure 1:
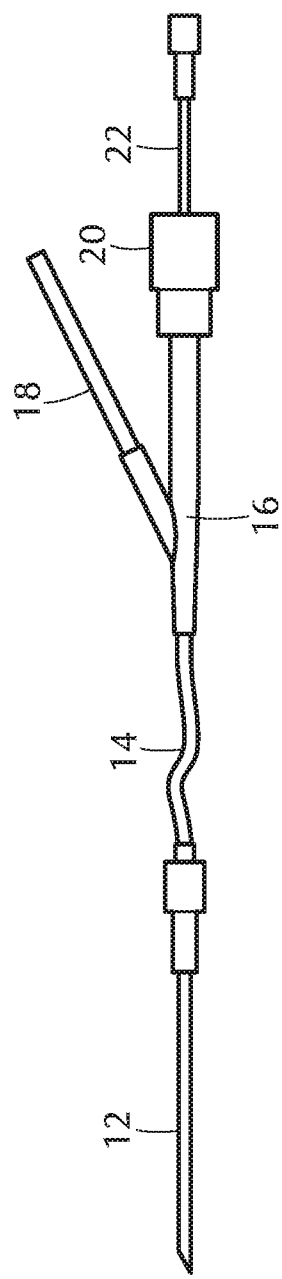
FIG. 1 is a plan view illustrating a portion of an exemplary intravenous (IV) infusion kit comprising tubing, an IV injection port, and connection.

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

A base polymeric formulation is a material from which a medical device may be made. Preferably, the base polymeric formulations utilized in conjunction with the polypropylene-poly(ethylene oxide) amphiphilic graft copolymers (PP-g-PEOs) disclosed herein comprise at least a polymer or co-polymer of propylene. Exemplary desirable base polymeric formulations include but are not limited to polypropylene, systems such as but not limited to polypropylene, polypropylene co-polymers including but not limited to a polypropylene-maleic anhydride co-polymer, polyethylene-polypropylene co-polymers, and/or polypropylene-containing thermoplastic elastomers (TPEs). The base formulation may further include other ingredients, independently selected from one or more of the following: reinforcing and non-reinforcing fillers, plasticizers, antioxidants, stabilizers, processing oil, extender oils, lubricants, antiblocking, antistatic agents, waxes, foaming agents, pigments, flame retardants and other processing aids known in the compounding art. Fillers and extenders which can be utilized include conventional inorganics such as calcium carbonate, clays, silica, talc, titanium dioxide, carbon black, and the like. The processing oils generally are paraffinic, naphthenic or aromatic oils derived from petroleum fractions. The oils are selected from those ordinarily used in conjunction with the specific plastics or rubbers present in the formulation.

Reference to polypropylene-poly(ethylene oxide) amphiphilic graft copolymers (PP-g-PEO) means that a graft copolymer is formed by a polypropylene-containing monomer or prepolymer and poly(ethylene oxide), resulting in at least a polypropylene backbone and PEO side chains. The polypropylene-containing monomer or prepolymer may provide a desired functionality or reactivity to accept side chains. The polypropylene-containing monomer or prepolymer may have a polypropylene backbone with pendant groups suitable to receive PEO. A non-limiting example of a polypropylene-containing prepolymer is a maleated polypropylene (also referred to as polypropylene-maleic anhydride co-polymer) (PP-MA).

Reference to "free poly(ethylene oxide)" means poly(ethylene oxide) that is not part of the polyethylene-poly(ethylene oxide) amphiphilic graft copolymers.

As used herein the term "connector" is understood to include any structure that is part of an intravenous device that is capable of making a connection with a secondary intravenous device. Non-limiting examples of connectors in accordance with the present invention include needleless connectors, male Luer connectors, female Luer connectors, side port valves, y-port valves, port valves, and other similar structures. Connectors are preferably formed from polar materials, which are those materials whose polymers have electrons that are not symmetrically distributed resulting in polymers having slightly positive sections and slightly negative sections. Exemplary polar materials include but are not limited to poly(methyl methacrylate) (PMMA), styrene maleic anhydride (SMA), polycarbonate (PC), and methyl methacrylate-acrylonitrile-butadiene-styrene (MABS).

An additive is a component added to a formulation which is not reactive within the formulation.

Principles and embodiments of the present invention relate generally to medical devices and components used therein made from a base polymeric formulation to which an additive comprising a polypropylene-poly(ethylene oxide) amphiphilic graft copolymer (PP-g-PEO) is added via melt process but can be incorporated via other mechanisms such dissolving in a compatible solvent. Methods of making and using these medical devices and components are also provided herein.

Embodiments of the present invention provide benefits over the prior art. For example, the disclosed invention here is a clean system in that there are no reactive agents involved in the process, which eliminates any concerns of un-reacted agents or residuals, especially for medical applications. In addition, the traditional solvent bonding process remains the same in that no further step is needed, such as a step of applying adhesives, either solvent based adhesive or bulk adhesive. Further, low amounts of additive achieve enhanced bonding. That is, the copolymer additive is present in the base polymeric formulation in an amount in the range of about 0.01 to about 5.0% by weight of the base polymeric formulation of the medical device component (e.g., tubing), which is not expected to have any impact on the component's final properties or the process to make the components. The PP-g-PEO copolymer has been designed to have an extremely hydrophobic segment PP and an extremely hydrophilic segment PEO. The PP-g-PEO copolymer enhanced the interfacial bonding strength between PP and a second polymer like PMMA, SMA, PC, and MABS at a loading of 0.5 wt.-%.

PP-g-PEO graft copolymers have two kinds of segments. The PP segments are miscible with a polyolefin such as polypropylene, and the PEO segments are miscible/compatible with second materials such as PMMA, SMA, PC, or MABS. When PP-g-PEO is melt blended with a polyolefin such as polypropylene, due to the hydrophilicity of the PEO segment, the graft copolymers tend to surge to the polymer surface and remain there, although at a low concentration or loading (for example, about 5 wt.-% or less, or about 1 wt.-% or less, or even about 0.5 wt.-% or less). This differentiates itself from other compatibilizer systems. When solvent bonding polyolefin (containing PP-g-PEO copolymers) with a second material, the PP segments stay in the polyethylene side, while the PEO segments entangle, or adhere/interact, with the second material, PMMA, SMA, PC, or MABS. The PP-PEO graft copolymers work as a chemical bridge connecting the otherwise immiscible polyethylene/second materials and improve the interfacial bonding strength.

Typically, reactive blending/compatibilization is preferred due to its superiority in enhancing mechanical performance. For pre-made copolymers, it would require minimum 5-10% loading by weight, in order to achieve compatibilization or mechanical performance improvement. For the PP-g-PEO system, an amount of about 5 wt.-% or less of the copolymer to achieves significant increase on interfacial bonding strength, which is unexpected. Without intended to be bound by theory, this can be explained due to the fact that polypropylene (PP) present in tubing material has extremely good miscibility with PP segments of the additive and the same time it is immiscible with PEO segment that causes separation of PEO segment from the dissimilar polymer matrix to the surface.

General Procedure for Synthesis of PP-g-PEO & Preparation of Blend with Base Polymer Formulation Polypropylene-poly(ethylene oxide) amphiphilic graft copolymers (PP-g-PEO) are additives for the base polymeric formulations of components of medical devices. These copolymers are also discussed in U.S. Pat. No. 9,150,674 to common assignee, which is incorporated herein by reference. The process to make amphiphilic graft copolymers involves grafting poly(ethylene oxide) onto maleated polypropylene platform using oxo-anion ring-opening polymerization chemistry. Polypropylene based graft copolymers are prepared starting from maleic anhydride grafted isotactic polypropylene. The amphiphilic character will result from the incorporation of hydrophilic poly(ethyleneoxide) (PEG) side-chains.

Preparation of amphiphilic polypropylene-based copolymers comprise: obtaining maleic anhydride grafted polypropylene wherein the molar percentages of grafted maleic anhydride units is in the range from 2 and 10 mole percent; the molar values of propylene units is in the range from 98 to 90 mole percent; reacting the maleic anhydride grafted polypropylene with a reducing agent to prepare a iPP-diol copolymer, wherein the diol content is equal to the molar percentage of the originally grafted maleic anhydride units:

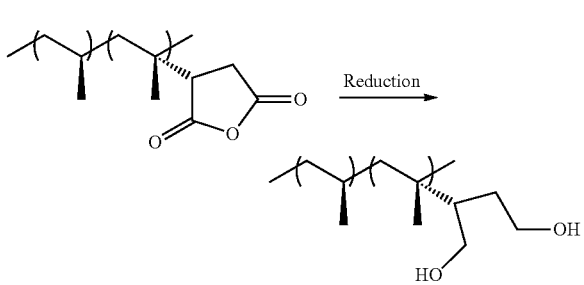

and subsequently performing ethylene oxide ring-opening polymerization on the iPP-diol copolymer; and isolating an amphiphilic iPP-g-PEO copolymer.

An exemplary PP-g-PEO copolymer is shown according to Formula (I).

Formula (I)

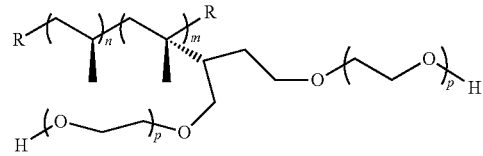

wherein R represents the end-groups present in either Ziegler-Natta or metallocene catalyzed polypropylene including, but not limited to, hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent; and p is in the range of 5 to 500. The amount of diol after reduction of the maleic anhydride may be in the range from 2 to 10 mole percent.

The molar percentage value of propylene may be in the range of from 90 to 98 mole percent, the molar percentage value of diol derived from reduction of maleic anhydride may be in the range of from 10 to 2 mole percent, and the molar percentage value of p may be in the range of from 5 to 400 mole percent.

In one or more embodiments, the ethylene oxide ring-opening polymerization is performed at a reaction temperature in the range of −20 to 150° C. In a specific embodiment, the ethylene oxide ring-opening polymerization is performed at a reaction temperature of greater than 30° C. In another specific embodiment, the ethylene oxide ring-opening polymerization is performed at a reaction temperature of 130° C.

The ethylene oxide ring-opening polymerization may performed under alkaline conditions. The ethylene oxide ring-opening polymerization may be performed using 1,3 propane sultone and/or triethylamine.

In one or more embodiments, the amphiphilic iPP-g-PEO copolymer has a dispersity index in the range of 2 to 8.

An exemplary PP-g-PEO copolymer composition is listed in Table 1.

TABLE 1

Exemplary PP-g-PEO copolymer

| Nomenclature (PP-g-PEO) | Average - $CH_2$—$CH_2$—$CH_2$— Interval Numbers (Brush Density) (n) | Average EO Units in Brush (p) |
|---|---|---|
| PP-g-PEO | <1 | 45.5 |

Addition of the polypropylene-poly(ethylene oxide) amphiphilic graft copolymer (PP-g-PEO) to the base polymeric formulation is done via melt processing. The term "melt processing" is used to mean any process in which polymers, such as the polyolefin, are melted or softened. Melt processing includes extrusion, pelletization, film blowing or casting, thermoforming, compounding in polymer melt form, fiber spinning, or other melt processes.

Any equipment suitable for a melt processing can be used as long as it provides sufficient mixing and temperature control. For instance, a continuous polymer processing system such as an extruder, a static polymer mixing device such as a Brabender blender, or a semi-continuous polymer processing system, such as a BANBURY mixer, can be used. The term "extruder" includes any machine for polyolefin and TPE extrusion. For instance, the term includes machines that can extrude material in the form of powder or pellets, sheets, fibers, or other desired shapes and/or profiles. Generally, an extruder operates by feeding material through the feed throat (an opening near the rear of the barrel) which comes into contact with one or more screws. The rotating screw(s) forces the polyolefin forward into one or more heated barrels (e.g., there may be one screw per barrel). In many processes, a heating profile can be set for the barrel in which three or more independent proportional-integral-derivative controller (PID)-controlled heater zones can gradually increase the temperature of the barrel from the rear (where the plastic enters) to the front. When a melt extrusion is used, the mixing can take place during the melt extrusion step. The heat produced during the extrusion step provides the energy necessary for the mixing between different components. A temperature at or above the melting temperature of the polymer may be maintained for a time sufficient to mix all the components. For instance, the mixing time may be at least 5 seconds, at least 10 seconds, or at least 15 seconds. Typically, the mixing time is 15-90 seconds.

Suitable blending temperature during melt mixing of polyolefins or TPE with an additive should be sufficient to melt or to soften the component of the composition which has the highest melting or softening point. The temperature typically ranges from 60 to 300° C., for instance, from 100 to 280° C., from 90 to 150° C. One skilled in the art understands that a polyolefin or TPE mixtures thereof typically melts or softs over a temperature range rather than sharply at one temperature. Thus, it may be sufficient that the polyolefin be in a partially molten state. The melting or softening temperature ranges can be approximated from the differential scanning calorimeter (DSC) curve of the polyolefin or mixtures thereof.

TABLE 2

Exemplary Formulations (with the proviso that the ingredients total 100%).

| Blend Ingredient | A by weight | B by weight | C by weight |
|---|---|---|---|
| Base Polymeric Formulation | 95-99.99% | 95-99.99% | 95-99.99% |
| Polypropylene | 50-100% | 0-50% | 0-50% |
| Polyethylene | 0-50% | 50-100% | 0-50% |
| Propylene-containing Thermoplastic elastomer (TPE) | 0-50% | 0-50% | 50-100% |
| Optional further ingredients | 0-10% | 0-10% | 0-10% |
| Polypropylene-poly(ethylene oxide) amphiphilic graft copolymer (PP-g-PEO) additive | 0.01-5% | 0.01-5% | 0.01-5% |

In one or more embodiments, including Exemplary Formulations A, B, and C, the polypropylene-poly(ethylene oxide) amphiphilic graft copolymer (PP-g-PEO) additive may be present in amounts of about 0.01 to about 5.0% by weight; about 0.1 to about 4.0% by weight; about 0.2 to about 2.0% by weight; about 0.25 to about 0.75% by weight; or about 0.5 weight %.

Suitable polyethylene-polypropylene co-polymers may include—reactor grade or melt blended mixtures of the polypropylene and polyethylene polyolefins with or without polyolefin elastomers (final formulation containing from but not limited to about 10 wt.-% up to about 80 wt.-% ethylene and/or propylene monomeric units). The term "blend" or "polymer blend" generally refers to a mixture of two or more components. Such a blend may or may not be miscible, and may or may not be phase separated.

Suitable polyolefins include those prepared from linear or branched olefins having 2 to 20 carbon atoms, 2 to 16 carbon atoms, or 2 to 12 carbon atoms. Typically, the olefin used to prepare the polyolefin is α-olefin. Exemplary linear or branched α-olefins includes, but are not limited to, ethylene, propylene, 1-butene, 2-butene, 1-pentene, 3-methyl-1-butene, 4-methyl-1-pentene, 3-methyl-1-pentene, 1-hexene, 3,5,5-trimethyl-1-hexene, 4,6-dimethyl-1-heptene, 1-octene, 1-decene, 1-undecene, 1-dodecene, 1-tetradecene, 1-hexadecene, 1-octadecene, and 1-eicocene. These olefins may contain one or more heteroatoms such as an oxygen, nitrogen, or silicon. The term "polyolefin" generally embraces a homopolymer prepared from a single type of olefin monomer as well as a copolymer prepared from two or more olefin monomers. A specific polyolefin referred to herein shall mean polymers comprising greater than 50% by weight of units derived from that specific olefin monomer, including homopolymers of that specific olefin or copolymers containing units derived from that specific olefin monomer and one or more other types of olefin comonomers. The polyolefin used herein can be a copolymer wherein the comonomer(s) is/are randomly distributed along the polymer chain, a periodic copolymer, an alternating copolymer, or a block copolymer comprising two or more homopolymer blocks linked by covalent bonds. Typical polyolefins include polyethylene, polypropylene, a copolymer of polyethylene and polypropylene, and a polymer blend containing polyethylene, polypropylene, and/or a copolymer of polyethylene and polypropylene. Polyolefin can also be an ethylene rich impact copolymer (may contain ethylene comonomer at the amount of at least 10 wt.-%; and up to 40 wt.-%), i.e., a heterophasic polyolefin copolymer where one polyolefin is the continuous phase and an elastomeric phase is uniformly dispersed therein. This would include, for instance, a heterophasic polypropylene copolymer where polypropylene is the continuous phase and an elastomeric phase is uniformly dispersed therein. The impact copolymer results from an in-reactor process rather than physical blending. The polyolefins mentioned above can be made by conventional Ziegler/Natta catalyst-systems or by single-site catalyst-systems.

Suitable polyolefin elastomers for use in the process of the invention include styrene ethylene butylene styrene (SEBS)-based elastomers, which include polypropylene. As used herein, the term "elastomer" refers to products having rubber-like properties and little or no crystallinity. Preferably, the polyolefin elastomers contain from about 10 wt.-% up to about 80 wt.-% propylene monomeric units. Illustrative polyolefin elastomers which are commercially available include Lanxess Corporation's BUNA EP T 2070 (22 Mooney ML(1+4) 125° C., 68% ethylene, and 32% propylene); BUNA EP T 2370 (16 Mooney, 3% ethylidene norbornene, 72% ethylene, and 25% propylene); BUNA EP T 2460 (21 Mooney, 4% ethylidene norbornene, 62% ethylene, and 34% propylene); ExxonMobil Chemical's VISTALON 707 (72% ethylene, 28% propylene, and 22.5 Mooney); VISTALON 722 (72% ethylene, 28% propylene, and 16 Mooney); and VISTALON 828 (60% ethylene, 40% propylene, and 51 Mooney). Suitable EP elastomers available from commercial sources also include ExxonMobil Chemical's VISTAMAXX series of elastomers, particularly VISTAMAXX grades 6100, 1100, and 3000. These materials are ethylene-propylene elastomers of 16, 15, and 11 wt.-% ethylene content, respectively, and a Tg of about −20 to −30° C. VISTAMAXX 6100, 1100, and 3000, respectively, have a melt flow rate of 3, 4, and 7 g/10 min at 2300° C.; a density of 0.858, 0.862, and 0.871 g/cm$^3$; and a 200 g Vicat softening point of 48, 47, and 64° C. Other suitable elastomers include Dow Chemical's VERSIFY propylene-ethylene copolymers, particularly grades DP3200.01, DP3300.01, and DP3400.01, which have nominal ethylene contents of 9, 12 and 15 wt.-%, respectively, and corresponding nominal propylene contents of 91, 88, and 85 wt.-%, respectively. These grades have a melt flow rate of 8 g/10 min at 230° C.; a density of 0.876, 0.866, and 0.858 g/cm$^3$, respectively; a Vicat softening point of 60, 29, and <20° C., respectively; and a Tg of −25, −28, and −31° C., respectively.

Preferably, the polyolefin elastomers contain from but not limited to about 10 wt.-% up to about 80 wt.-% propylene monomeric units. The term "thermoplastic elastomer" (TPE) in general defines blends of polyolefins and rubbers in which blends of the rubber phase is not cured, i.e., so called thermoplastic olefins (TPO), blends of polyolefins and rubbers in which blends of the rubber phase has been partially or fully cured by a vulcanization process to form thermoplastic vulcanizates (TPV), or unvulcanized block-copolymers or blends thereof. Non-polar thermoplastic elastomer may made from a thermoplastic polyolefin homopolymer or copolymer, and an olefinic rubber which is fully crosslinked, partially crosslinked or not crosslinked, and optionally commonly used additives; as well as a block-copolymer of styrene/conjugated diene/styrene and/or its fully or partially hydrogenated derivative.

Polyolefins suitable for use in TPE composition include thermoplastic, crystalline polyolefin homopolymers and copolymers. They are desirably prepared from monoolefin monomers having but not limited to 2 to 7 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth)acrylates and/or vinyl acetates. The polyolefins which can be used in TPE formulations can be any desired grade of polypropylene including isotactic polypropylene. Functionalized polypropylene is also desirable including, for example, polypropylene-maleic anhydride copolymer. Polyolefins can be made by conventional Ziegler/Natta catalyst-systems or by single-site catalyst-systems, or other polyolefin catalyst technology in combination with various process technologies and solutions.

Suitable olefinic rubbers of the monoolefin copolymer rubbers comprise non-polar, rubbery copolymers of two or more α-monoolefins, preferably copolymerized with at least one polyene, usually a diene. Saturated monoolefin copolymer rubber, for example ethylene-propylene copolymer rubber (EPM) can be used. However, unsaturated monoolefin rubber such as EPDM rubber is more suitable. EPDM is a terpolymer of ethylene, propylene and a non-conjugated diene. Satisfactory non-conjugated dienes include 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; dicyclopentadiene (DCPD) and vinyl norbornene (VNB). Butyl rubbers are also used in TPE formulation. The term "butyl rubber" includes copolymers of an isoolefin and a conjugated monoolefin, terpolymers of an isoolefin with or without a conjugated monoolefin, divinyl aromatic monomers and the halogenated derivatives of such copolymers and terpolymers. Another suitable copolymer within the olefinic rubber is a copolymer of a $C_{4-7}$ isomonoolefin, and a para-alkylstyrene. A further olefinic rubber used in TPE is natural rubber. The main constituent of natural rubber is the linear polymer cis-1,4-polyisoprene. Furthermore polybutadiene rubber and styrene-butadiene-copolymer rubbers can also be used. Blends of any of the above olefinic rubbers can be employed, rather than a single olefinic rubber. Further suitable rubbers are nitrite rubbers. Examples of the nitrile group-containing rubber include a copolymer rubber comprising an ethylenically unsaturated nitrile compound and a conjugated diene. Further, the copolymer rubber may be one in which the conjugated diene units of the copolymer rubber are hydrogenated. Specific examples of the ethylenically unsaturated nitrile compound include acrylonitrile, α-chloroacrylonitrile, α-fluoroacrylonitrile and methacrylonitrile. Among them, acrylonitrile is particularly preferable. Other suitable rubbers are based on polychlorinated butadienes such as polychloroprene rubber. These rubbers are commercially available under the trade names Neoprene® and Bayprene®.

A commercially available thermoplastic elastomer (TPE) that showed some benefits with the addition of PP-g-PEO is one formulated without plasticizers having a nominal density of 0.888 g/cm$^3$ (ASTM D792-13) and a nominal composition of: 33.0 mol % propylene, 24.8 mol % ethylene, and 42.2 mol % butylene.

Base polymeric materials with PP-g-PEO additive prepared with according to the process of the invention may be formed into useful articles by standard forming methods known in the art, e.g., by blown film extrusion, cast film extrusion, injection or blow molding, pelletizing, foaming, thermoforming, compounding in polymer melt form, or fiber spinning. For example, any technique discussed above in the embodiments describing the melt processes can be used to prepare modified polymer, thereby forming various useful articles, depending on the type of melt processing technique used. For instance, blend may be used in making films, such as blown or cast films. The techniques of blown film extrusion and cast film are known to one skilled in the art in the area of production of thin plastic films. Polymers with PP-g-PEO additive may also be used in coextruded films. The formation of coextruded blown films is known to one skilled in the art. The term "coextrusion" refers to the process of extruding two or more materials through a single die with two or more orifices arranged such that the extrudates merged together into a laminar structure, for instance, before chilling or quenching.

Turning to FIG. 1, a portion of an intravenous (IV) infusion kit comprising tubing, an IV injection port, and connection is illustrated. A patient is connected to an IV source by means of an intravenous (IV) infusion kit. The kit comprises a length of tubing having connectors on the ends and one or more injection sites or ports. The injection sites or ports enable the injection of additional medications or the like via a syringe or other IV source. The exemplary kit, as illustrated, comprises a needle 12 for insertion into a patient connected to tubing 14 having a Y-site (connector) 16, and a tubing branch 18 for connection to a source of IV fluid (not shown). The Y-site includes a conventional IV injection site or port comprising an elastic plug and cap combination 20 of Neoprene or the like on or over the end of a portion of the Y-tube. The connection of an additional IV source for the injection of a fluid is accomplished by inserting a conventional needle 22 through the site or port 20 into the underlying tube. Embodiments of the present invention include tubing 14 being formed from a base polymeric formulation comprising a polyolefin (e.g., polyethylene or polypropylene) or a thermoplastic elastomer (TPE) to which is added an additive comprising a polypropylene-poly(ethylene oxide) amphiphilic graft copolymer (PP-g-PEO). The Y-site (connector) 16 may be formed from a material selected from the group consisting of: poly(methyl methacrylate) (PMMA), styrene maleic anhydride (SMA), polycarbonate (PC), and methyl methacrylate-acrylonitrile-butadiene-styrene (MABS). The tubing 14 is solvent-bonded to the Y-site (connector) 16.

General Procedure for Solvent Bonding

The solvent for treating outer surface of the tube is typically selected from one or more hydrocarbons, such as cyclohexanone, cyclohexane, hexane, xylene, toluene, tetrahydrofuran (THF), ethyl acetate (EA) and methyl ethyl ketone (MEK). Solvent treatment typically comprises applying the solvent to surface of the end portion of tube prior to inserting the end portion into the axial passage of the tubular body of the connector.

Solvent bonding is a method that allows two or more materials to be bonded together without the use of an adhesive. For example, Material "A" is a first component, such as tubing, that needs to be permanently affixed (or bonded) to Material "B", which may be a connector. Both Materials "A" and "B" are dipped into a solvent that is suitable for processing of medical devices. The materials are then overlapped and secured (e.g., by clamping) to form a bond area. The materials are kept in contact with each other for a time suitable to allow the overlapped area to cure and form a bond.

Solvents suitable for assembling medical devices include but are not limited to: cyclohexanone, methylene chloride, methyl ethyl ketone (MEK), tetrahydrofuran, acetone, 1,2-dichloroethane, methyl benzene, tetrahydrofuran and blends of the solvents (50/50% methylene chloride/cyclohexanone, 50/50% or 80/20% MEK/cyclohexanone); bonding solvent can be further loaded up to 25% by weight with the parent plastic or component of base formulation material (of the tube or connector) to increase viscosity.

EMBODIMENTS

Various embodiments are listed below. It will be understood that the embodiments listed below may be combined with all aspects and other embodiments in accordance with the scope of the invention.

Embodiment 1

A tubing for a medical device formed from a blend comprising: a base polymeric formulation comprising at least a polymer or co-polymer of ethylene or propylene and excluding free poly(ethylene oxide); and an additive comprising a polypropylene-poly(ethylene oxide) amphiphilic graft copolymer (PP-g-PEO); the PP-g-PEO being present in the blend in an amount in the range of about 0.01 to about 5.0% by weight of the blend.

Embodiment 2

The tubing of embodiment 1, wherein the PP-g-PEO is according to Formula (I):

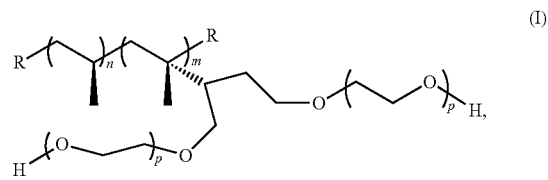

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

Embodiment 3

The tubing of one of embodiments 1 to 2, wherein the base polymeric formulation comprises polyethylene, polypropylene, a polypropylene-maleic anhydride co-polymer, a polyethylene-polypropylene co-polymer, a polyethylene- and/or polypropylene-containing thermoplastic elastomer (TPE), or combinations thereof.

Embodiment 4

The tubing of one of embodiments 1 to 3, wherein the base polymeric formulation comprises a co-polymer of polyethylene and polypropylene.

Embodiment 5

The tubing of one of embodiments 1 to 3, wherein the polyethylene-and/or polypropylene-containing thermoplastic elastomer (TPE) comprises at least 60 mol % total polyethylene and/or polypropylene.

Embodiment 6

The tubing of any one of embodiments 1 to 5, wherein the PP-g-PEO is a product of ethylene oxide ring-opening polymerization of a polypropylene-maleic anhydride co-polymer (PP-MA) having from 10-50 weight percent of maleic anhydride.

Embodiment 7

A medical device comprising: a tubing comprising a polymeric blend comprising a base polymeric formulation comprising at least a polymer or co-polymer of ethylene or propylene and excluding free poly(ethylene oxide), and an additive comprising a polypropylene-poly(ethylene oxide) amphiphilic graft copolymer (PP-g-PEO) according to Formula (I); wherein the PP-g-PEO is present in the blend in an amount in the range of about 0.01 to about 5.0% by weight of the blend; and a connector bonded to the tubing; wherein the PP-g-PEO is effective to enhance bonding of the tubing to a connector.

Embodiment 8

The medical device of embodiment 7, wherein the base polymeric formulation comprises polyethylene, polypropylene, a polyethylene-polypropylene co-polymer, a polyethylene- and/or polypropylene-containing thermoplastic elastomer (TPE), or combinations thereof.

Embodiment 9

The medical device of one of embodiments 7 to 8, wherein the base polymeric formulation comprises a co-polymer of polyethylene and polypropylene.

Embodiment 10

The medical device of one of embodiments 7 to 8, wherein the polyethylene-and/or polypropylene-containing thermoplastic elastomer (TPE) comprises at least 60 mol % polyethylene and/or polypropylene.

Embodiment 11

The medical device of one of embodiments 7 to 10, wherein the PP-g-PEO is a product of ethylene oxide ring-opening polymerization of a polypropylene-maleic anhydride co-polymer (PP-MA) having from 10-50 weight percent of maleic anhydride.

Embodiment 12

The medical device of one of embodiments 7 to 11, wherein the connector comprises a polar material.

Embodiment 13

The medical device of embodiment 12, wherein the polar material selected from the group consisting of: poly(methyl methacrylate) (PMMA), styrene maleic anhydride (SMA), polycarbonate (PC), and methyl methacrylate-acrylonitrile-butadiene-styrene (MABS).

Embodiment 14

The medical device of one of embodiment 7 to 13, wherein the connector is solvent-bonded to the tubing.

Embodiment 15

A method of making a medical device comprising: obtaining a polypropylene-poly(ethylene oxide) amphiphilic graft copolymer (PP-g-PEO); combining the PP-g-PEO with a base polymeric formulation comprising at least a polymer or co-polymer of ethylene or propylene and excluding free poly(ethylene oxide) to form a blend, the PP-g-PEO being present in the blend in an amount in the range of about 0.01 to about 5.0% by weight of the blend; forming a tubing from the blend; bonding the tubing to a connector in the presence of a solvent to form the medical device; wherein the PP-g-PEO is effective to enhance bonding of the tubing to a connector.

Embodiment 16

The method of embodiment 15, wherein ethylene oxide ring-opening polymerization of a polypropylene-maleic anhydride co-polymer (PP-MA) having from 10-50 weight percent of maleic anhydride is used to form the PP-g-PEO, which is according to Formula (I).

Embodiment 17

The method of one of embodiments 15 to 16, wherein the base polymeric formulation comprises polyethylene, polypropylene, a polyethylene-polypropylene co-polymer, a polyethylene- and/or polypropylene-containing thermoplastic elastomer (TPE), or combinations thereof.

Embodiment 18

The method of one of embodiments 15 to 17, wherein the base polymeric formulation comprises a co-polymer of polyethylene and polypropylene.

Embodiment 19

The method of one of embodiments 15 to 17, wherein the polyethylene-and/or polypropylene-containing thermoplastic elastomer (TPE) comprises at least 60 mol % polyethylene and/or polypropylene.

Embodiment 20

For any embodiment 1 to 19, wherein the PP-g-PEO has a dispersity index in the range of 2 to 8.

EXAMPLES

PP-g-PEO graft copolymers tested herein are prepared according to the methods of U.S. Pat. No. 9,150,674. Specifically, polypropylene based graft copolymers were prepared from a polypropylene-maleic anhydride co-polymer (PP-MA) starting material. Controlled ring-opening polymerization was used to graft polymer side chains of ethylene oxide onto the polypropylene backbone to prepare polypropylene-graft-poly(ethylene oxide) (PP-g-PEO) copolymers having functionalized side groups. Incorporation of hydrophilic poly(ethylene oxide) (PEO) side-chains onto the polypropylene backbone resulted a copolymer with desired amphiphilic characteristics.

More specifically, the amphiphilic graft copolymers of the present invention were prepared in a two-step synthetic sequence. First, a reduction reaction was performed on the PP-MA platform to prepare an iPP-diol copolymer, wherein the diol content is equal to the molar percentage of the originally grafted maleic anhydride units. In the second step of the process, ethylene oxide ring-opening polymerization was performed on the iPP-diol copolymer to produce polypropylene based graft-copolymers.

The PP-g-PEO used in the following examples had a Brush Density of <1; an average EO units in Brush of 45.5; and a PEO content of ~16 wt. %.

Example 1

Comparative

A first base polymer formulation based on a commercially available thermoplastic elastomer (TPE) only was prepared. The TPE was analyzed by 13C-NMR and FTIR to contain 33.0 mol % propylene, 24.8 mol % ethylene, and 42.2 mol % butylene. A 2.5"×0.5" compression molded sample was prepared from the first base polymer formulation at 200° C.

Example 2

Blends of varying PP-g-PEO graft copolymer content were made by melt mixing the PP-g-PEO graft copolymer with the first base polymer formulation of Example 1, the graft copolymer being present in amounts of 0.5 wt.-% (Example 2-1) and 5 wt.-% (Example 2-2) by weight of the blend. Exemplary components of medical devices were prepared by compression molding as set forth in Example 1.

Example 3

Testing
  Solvent Bonding Procedure.
  Each of the exemplary components of medical devices according to Examples 1-2 (Material "A") was solvent bonded to an exemplary second component of a medical device (Material "B") made from polycarbonate (PC) (Makrolon® 2558). Materials "A" and "B" were both dipped into a cyclohexanone solvent (for ~5 seconds) and then overlapped (~0.75-1 in) to create a bond area. Samples were then clamped together and allowed to dry and harden for 48 hours.

Figure 2:
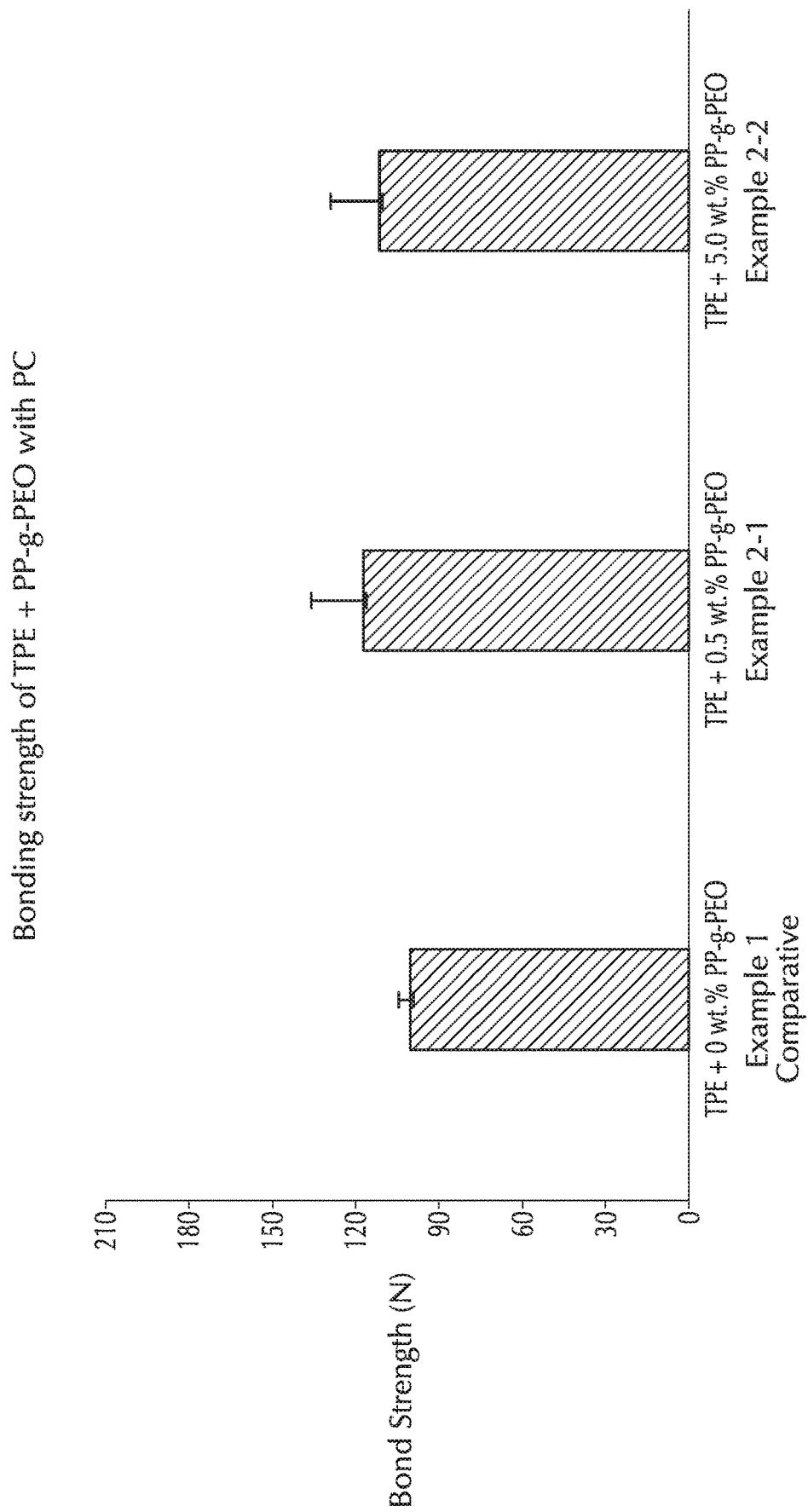
FIG. 2 provides a graph of bond strength (N) versus PP-g-PEO concentration (weight %) for Comparative Example 1 (0%) and Examples 2-1 (0.5%) and 2-2 (5.0%)

Bonded strength was measured using Instron mechanical testing instrument. Sample dimensions were measured to be 0.1 inches thick, 0.5 inches wide, and a strain rate of 1.5 mm/min was applied using 5 kN load cell. Samples were pulled until the bonded specimens "delaminated" and were separated from one another. The maximum force achieved before failure was recorded for each bonded sample. Five samples were tested for each composition and average values are reported in FIG. 2, which shows Bond Strength (N) versus PP-g-PEO content. Modest increases in bond strength (11-17%) were achieved by Examples 2-1 and 2-2.

Example 4

Effect of polyethylene (PE) content on bond strength of the TPE according to Examples 1-2 was determined. Varying amounts of PE were added to the TPE in combination with 0.5 wt. % PE760-g-PEO4, which was a polyethylene-poly(ethylene oxide) amphiphilic graft copolymers (PE-g-PEO) was made according to U.S. Pat. No. 9,150,674 by First, a hydrolysis reaction was performed on an ethylene vinyl alcohol (EVA) platform whereby the acetate units were removed to produce ethylene vinyl alcohol copolymers (EVOH) and a methyl acetate co-product. The acetate units were be removed by reaction with potassium methoxide and the co-product methyl acetate will be removed by distillation. The resultant polymeric potassium alkoxide was then used to initiate ethylene oxide ring-opening polymerization (ROP). In the second step of the process, oxo-anion polymerization was performed on the copolymers of ethylene and vinyl acetate to produce polyethylene based graft-copolymers. The PE760-g-PEO4 had a Brush Density of 36 and an average EO units in Brush of 145.

Exemplary components of medical devices were prepared by compression molding as set forth in Example 1. These components were solvent bonded to samples of PC, MABS, and PMMA connector materials in accordance with Example 3 and tested for bond strength.

Figure 3:
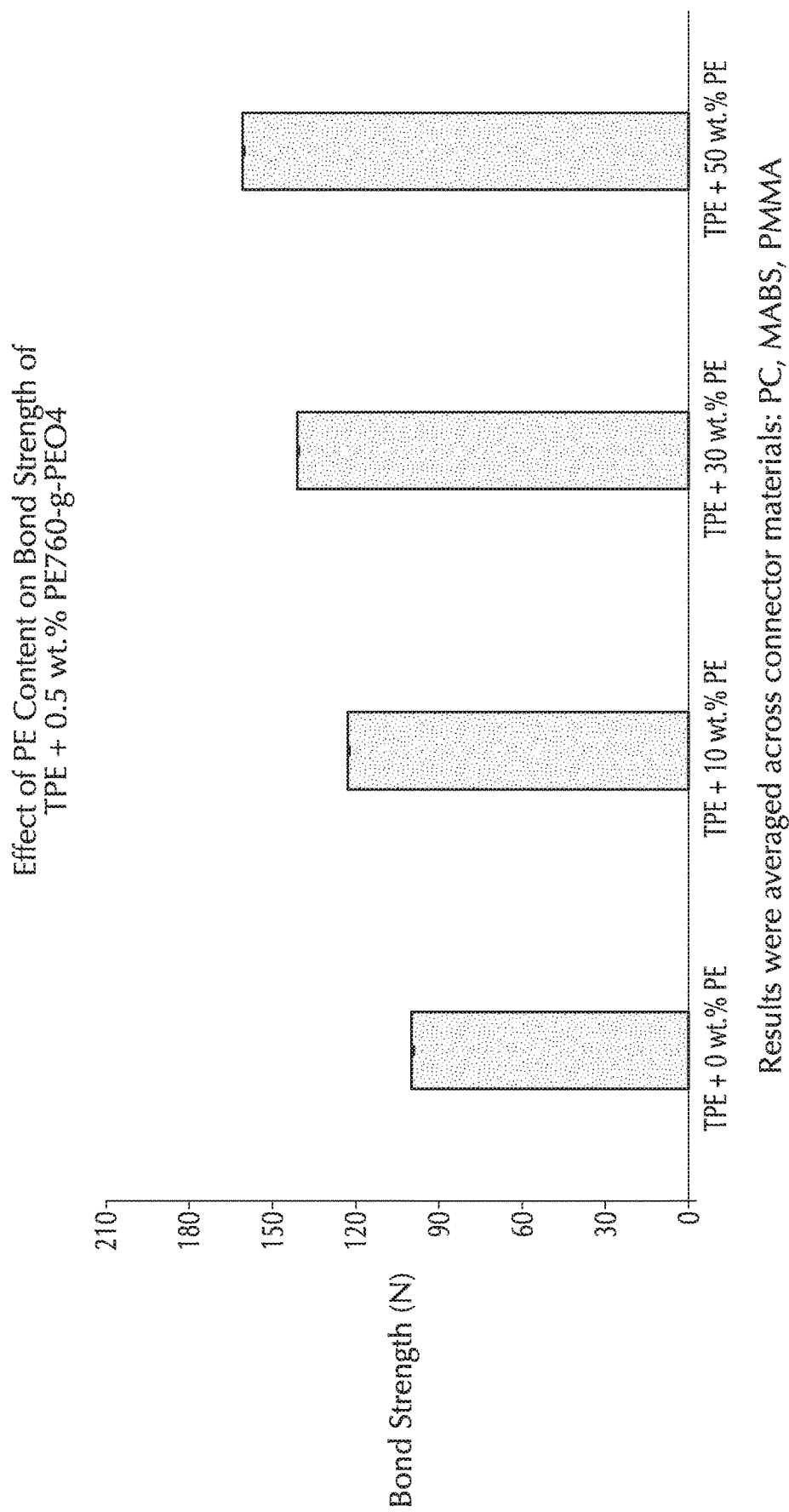
FIG. 3 is a graph of bond strength (N) versus PE concentration in an exemplary TPE base formulation, which used 0.5 wt.-% of PE-760-g-PEO-4 as the additive in the base formulation.

FIG. 3 provides a graph of bond strength (N) as averaged over the different connector materials versus PE concentration in an exemplary TPE base formulation, which used 0.5 wt.-% of PE-760-g-PEO-4 as the additive in the base formulation. From FIG. 3, it appears that a co-polymer PE-g-PEO is more effective when TPE is polyethylene (PE) or polypropylene (PP) rich. After addition of 10% PE to TPE bonding strength of [TPE+0.5 wt. % PE-g-PEO] sample increased by 23%. Grafted copolymers show solvent bonding strength increase for PP and PE rich TPE samples; suggesting that co-polymers are more effective in TPEs containing at least 30-40 mol % or higher of each of propylene (C3) and/or ethylene (2) single component (TPE should be C3 or C2 rich).

From this, it is concluded that a TPE is polyethylene (PE) or polypropylene (PP) rich will also be more effective when used with a co-polymer PP-g-PEO as disclosed herein. A preferred base polymeric formulation contains 60-100 mol % (or 65-100 mol % or even 70-100 mol %) total of polyethylene and polypropylene.

Example 5

Comparative

A second base polymer formulation based on a commercially available polypropylene (PP) (Homopolymer PH592) only was prepared. Exemplary components of medical devices were prepared by compression molding as set forth in Example 1.

Example 6

Blends of varying PP-g-PEO graft copolymer content were made by melt mixing the PP-g-PEO graft copolymer with the second base polymer formulation of Example 5, the graft copolymer being present in amounts of 0.5 wt.-% (Example 6-1) and 5 wt.-% (Example 6-2) by weight of the blend. Exemplary components of medical devices were prepared by compression molding as set forth in Example 1.

Example 7

Testing
  The solvent bonding procedure and testing according to Example 3 were conducted for the exemplary components of medical devices according to Examples 5-6 (Material "A"), which were solvent bonded to an exemplary second component of a medical device (Material "B") made from polycarbonate (PC) (Makrolon® 2558).

Figure 4:
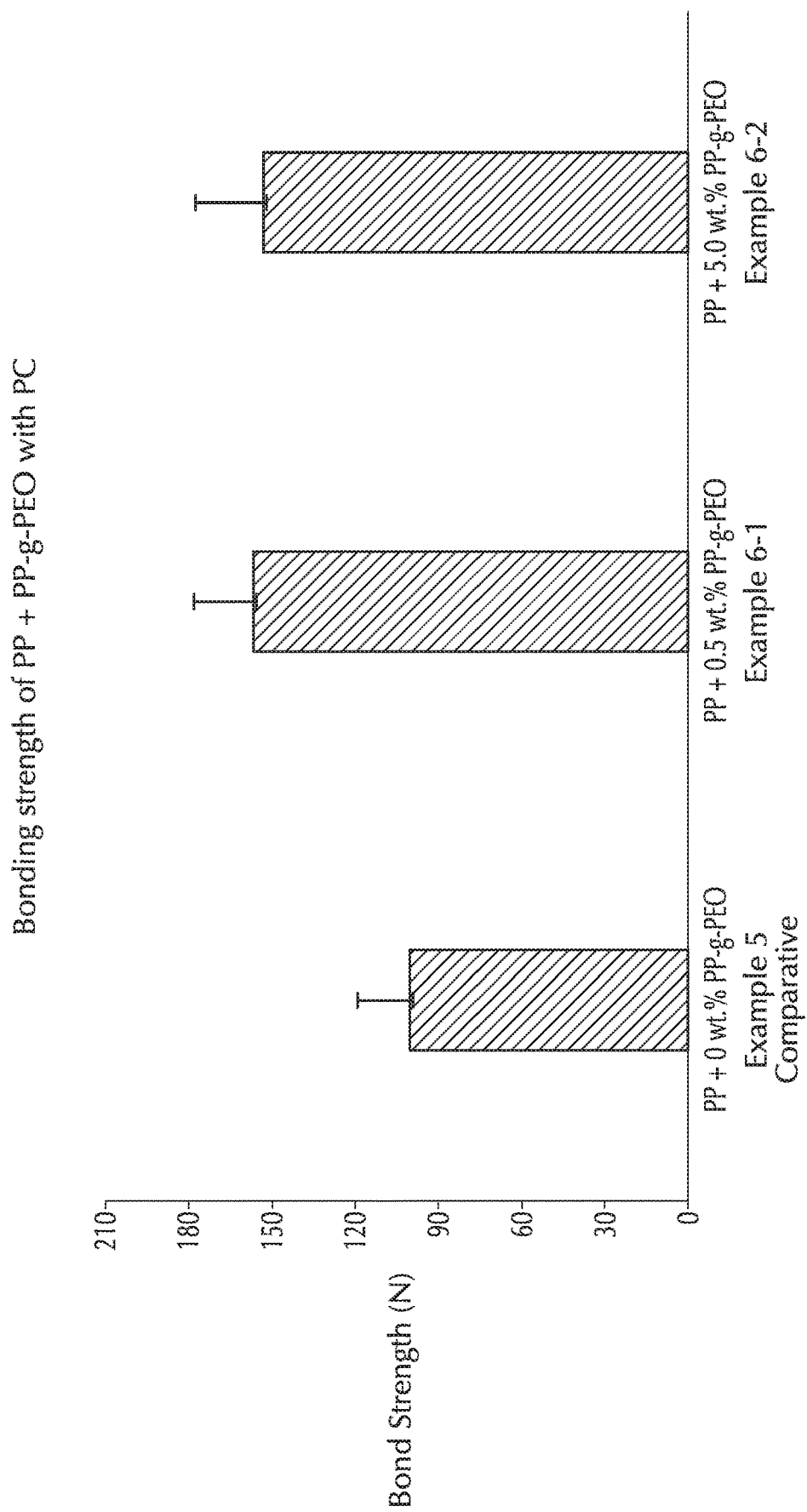
FIG. 4 provides a graph of bond strength (N) versus PP-g-PEO concentration (weight %) for Comparative Example 5 (0%) and Examples 6-1 (0.5%) and 6-2 (5.0%)

Average values are reported in FIG. 4, which shows Bond Strength (N) versus PP-g-PEO content. A significant increase in bond strength was achieved by Examples 6-1 (54%) and 6-2.

Example 8

Comparative

A third base polymer formulation based on a commercially available linear low density polyethylene (LLDPE) (Dowlexr 2045.01 G) only was prepared. Exemplary components of medical devices were prepared by compression molding as set forth in Example 1.

Example 9

Blends of varying PP-g-PEO graft copolymer content were made by melt mixing the PP-g-PEO graft copolymer with the third base polymer formulation of Example 8, the graft copolymer being present in amounts of 0.5 wt.-% (Example 9-1) and 5 wt.-% (Example 9-2) by weight of the blend. Exemplary components of medical devices were prepared by compression molding as set forth in Example 1.

Example 10

Testing

The solvent bonding procedure and testing according to Example 3 were conducted for the exemplary components of medical devices according to Examples 8-9 (Material "A"), which were solvent bonded to an exemplary second component of a medical device (Material "B") made from polycarbonate (PC) (Makrolon® 2558).

Figure 5:
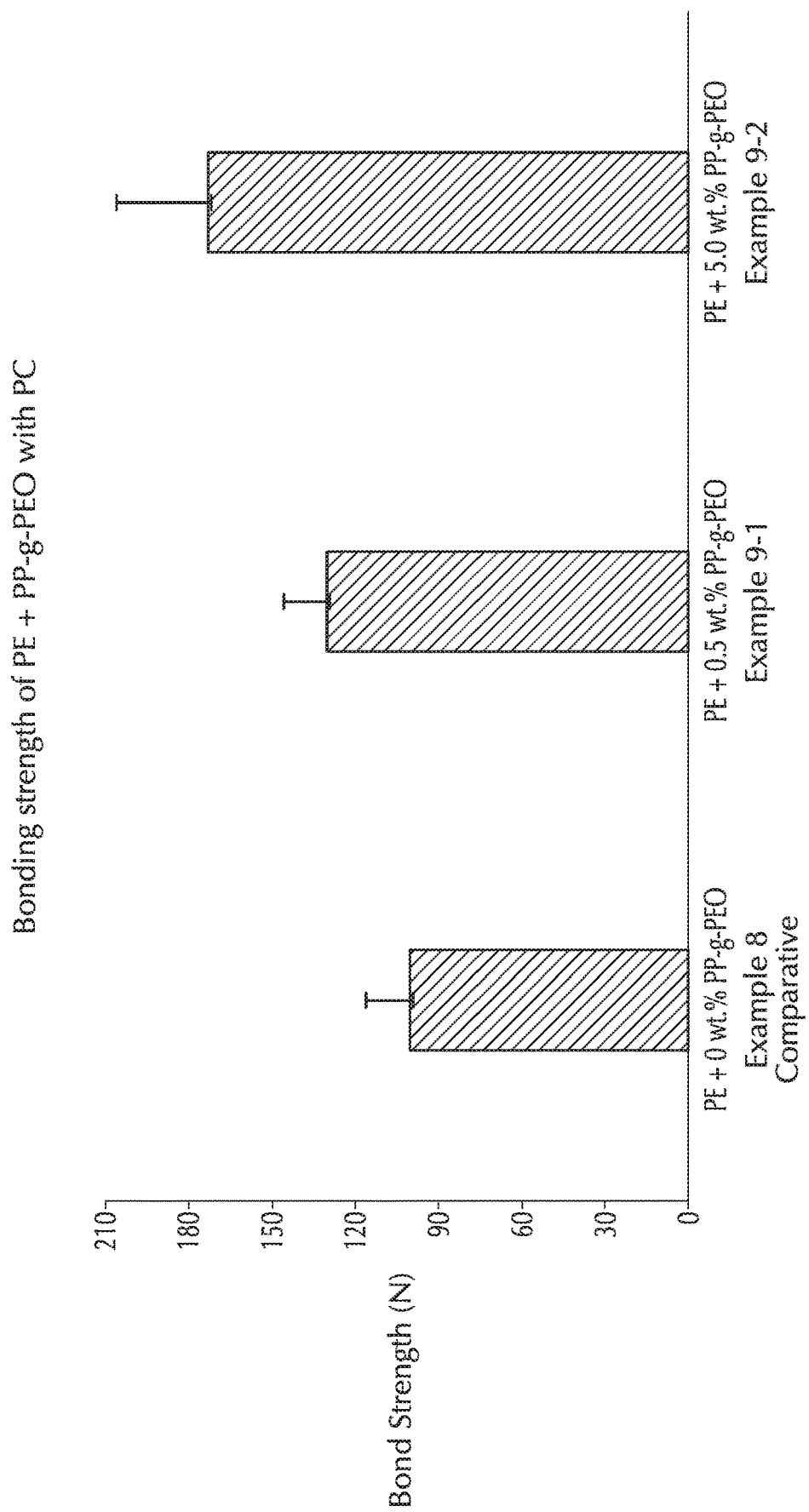
FIG. 5 provides a graph of bond strength (N) versus PP-g-PEO concentration (weight %) for Comparative Example 8 (0%) and Examples 9-1 (0.5%) and 9-2 (5.0%).

Average values are reported in FIG. 5, which shows Bond Strength (N) versus PP-g-PEO content. A significant increase in bond strength was achieved by Examples 9-1 (30%) and 9-2.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A tubing for a medical device formed from a blend comprising:
a base polymeric formulation comprising: from 10% to 50% by weight of a polyethylene homopolymer; and a thermoplastic elastomer (TPE) comprising a copolymer of polypropylene monomeric units with other monomeric units; wherein the base polymeric formulation excludes free poly(ethylene oxide); and
an additive comprising a polypropylene-poly(ethylene oxide) amphiphilic graft copolymer (PP-g-PEO copolymer), the PP-g-PEO copolymer being effective to enhance solvent bonding of the tubing to a connector;
wherein the other monomeric units of the thermoplastic elastomer (TPE) comprise ethylene and butylene monomeric units, wherein a total of propylene, ethylene, and butylene monomeric units is 100 mol %.

2. The tubing of claim 1, wherein the PP-g-PEO copolymer is present in the blend in an amount in the range of 0.01 to 2.5% by weight of the blend.

3. The tubing of claim 1, wherein the PP-g-PEO copolymer is according to Formula (I):

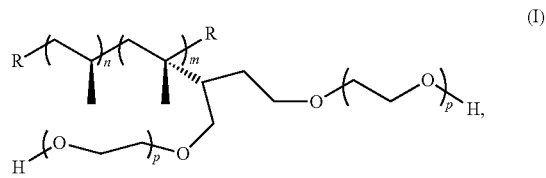

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

4. The tubing of claim 1, wherein the thermoplastic elastomer (TPE) comprises ethylene and propylene monomeric units in a total amount of at least 57 mol %.

5. A medical device comprising:
the tubing of claim 1; and
a connector bonded to the tubing;
wherein the PP-g-PEO copolymer is effective to enhance solvent bonding of the tubing to the connector.

6. The medical device of claim 5, wherein the thermoplastic elastomer (TPE) comprises ethylene and propylene monomeric units in a total amount of at least 57 mol %.

7. The medical device of claim 5, wherein the PP-g-PEO copolymer is according to Formula (I):

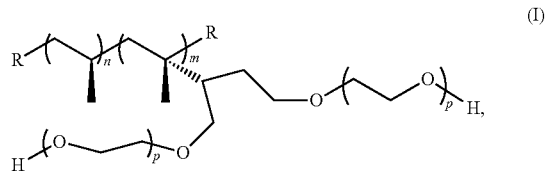

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

8. The medical device of claim 5, wherein the connector comprises a polar material selected from the group consisting of: poly(methyl methacrylate) (PMMA), styrene maleic anhydride (SMA), polycarbonate (PC), and methyl methacrylate-acrylonitrile-butadiene-styrene (MABS).

9. A medical tubing manufactured by a process comprising:
melting a polymeric base comprising: from 10% to 50% by weight of a polyethylene homopolymer; a thermoplastic elastomer (TPE) comprising a copolymer of propylene monomeric units with other monomeric units, the other monomeric units of the thermoplastic elastomer (TPE) comprising ethylene and butylene monomeric units, wherein a total of propylene, ethylene, and butylene monomeric units is 100 mol %; and excluding free poly(ethylene oxide) at a temperature in the range of 60° C. to 300° C. to form a melted polymeric base;
adding an additive comprising a polypropylene-poly(ethylene oxide) amphiphilic graft copolymer (PP-g-PEO copolymer) to the melted polymeric base to form a blend the PP-g-PEO copolymer being present in the blend in an amount in the range of 0.01 to 2.5% by weight of the blend; mixing the blend for a time period in the range of 15 seconds to 90 seconds; and
melt extruding the blend to form the tubing.

10. The medical tubing of claim 9, wherein the PP-g-PEO copolymer is according to Formula (I):

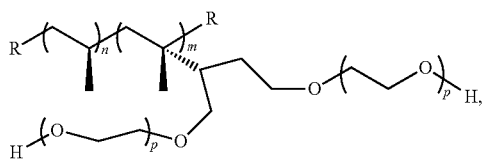

(I)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

11. The medical tubing of claim 9, wherein the thermoplastic elastomer (TPE) comprises ethylene and propylene monomeric units in a total amount of at least 57 mol %.

12. A method of making a medical device comprising:
obtaining a polypropylene-poly(ethylene oxide) amphiphilic graft copolymer (PP-g-PEO);
combining the PP-g-PEO with a base polymeric formulation comprising: from 10% to 50% by weight of a polyethylene homopolymer; and a thermoplastic elastomer (TPE) comprising a copolymer of polypropylene monomeric units with other monomeric units, the other monomeric units of the thermoplastic elastomer (TPE) comprising ethylene and butylene monomeric units, wherein a total of propylene, ethylene, and butylene monomeric units is 100 mol %, and excluding free poly(ethylene oxide) to form a blend, the PP-g-PEO being present in the blend in an amount in the range of about 0.01 to about 5.0% by weight of the blend;
forming a tubing from the blend;
bonding the tubing to a connector in the presence of a solvent to form the medical device;
wherein the PP-g-PEO is effective to enhance bonding of the tubing to a connector.

13. The method of claim 12, wherein ethylene oxide ring-opening polymerization of a polypropylene-maleic anhydride co-polymer (PP-MA) having from 10-50 weight percent of maleic anhydride is used to form the PP-g-PEO, which is according to Formula (I):

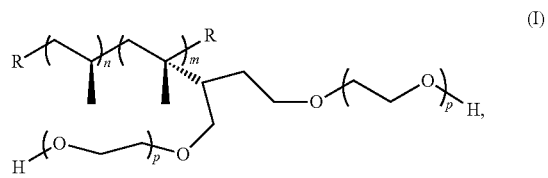

(I)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

14. The method of claim 12, wherein the thermoplastic elastomer (TPE) comprises ethylene and propylene monomeric units in a total amount of at least 57 mol %.

15. The method of claim 12, wherein the thermoplastic elastomer (TPE) comprises ethylene, propylene, butylene monomeric units in an amount of 100 mol %, and the PP-g-PEO copolymer is present in the blend in an amount in the range of 0.01 to 2.5% by weight of the blend.

16. The method of claim 12, wherein:
combining the PP-g-PEO copolymer with the base polymeric formulation comprises:
melting the base polymeric formulation at a temperature in the range of 60° C. to 300° C. to form a melted polymeric base and mixing the blend for a time period in the range of 15 seconds to 90 seconds; and
forming the tubing comprises melt extruding the blend.

* * * * *